(12) United States Patent
Dao

(10) Patent No.: US 7,157,242 B1
(45) Date of Patent: Jan. 2, 2007

(54) METHOD FOR STAINING FUNGI AND PROTOZOA

(75) Inventor: My Lien Dao, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 257 days.

(21) Appl. No.: 10/249,663

(22) Filed: Apr. 29, 2003

Related U.S. Application Data

(60) Provisional application No. 60/319,214, filed on Apr. 29, 2002.

(51) Int. Cl.
*C12Q 1/02* (2006.01)
*C12Q 1/18* (2006.01)
*C12N 1/00* (2006.01)

(52) U.S. Cl. .......................... 435/29; 435/34; 435/243; 435/40.5; 435/40.51

(58) Field of Classification Search ................. 435/34, 435/29, 243, 40.5, 40.51
See application file for complete search history.

(56) References Cited

U.S. PATENT DOCUMENTS 6,344,340 B1 * 2/2002 Dibner et al. .................. 435/29

OTHER PUBLICATIONS

Murray et al., "Manual of Clinical Microbiology", 6th edition ASM Press 1995, p. 37.*
Ge et al., Infection and Immunity, May 2001, p. 3502-3506, vol. 69, No. 5.□□*
Weiss et al.; Pages from The Microsporidia and Microsporifiosis; American Society for Microbiology.
Ignatius et al.; Comparative Evaluation of Modified Trichrome and Uvitex 2B Stains for Detection of Low . . . ; Journal of Clinical Microbiology; vol. 35, No. 9 p. 226-2269; Sep. 1997.
Ruchel et al.; Versatile Fluorescent Staining of Fungi in CLinical Specimens by Using the Optical Brightener Blankophor; Journal of Clinical Microbiology; vol. 37, No. 8 p. 2694-2696; 1999.
Green et al.; Discrimination Between Viable & Dead *Encephalitozoon cuniculi* Spores by Dual Stainging w/Sytox Green and Calcofluor . . . ; Journal of Clinical Microbiology; vol. 38, No. 10; 2000.
Kay et al.; Spectral Changes in a Cationic Dye Due to Interaction w/Macromolecules; Journal of Physical Chemistry; 68, p. 1896-1906; 1964.
Green et al.; Differential Stainging of Phosphoproteins on Polyacrylamide Gels w/Cationic Carbocyanine Dye; Analytical Biochemistry; 56, p. 43-51; 1973.
Green; Simultaneous Differential Staining of Nucleic Acids, Proteins, Conjugated Proteins and Polar Lipids by a Cationic Carbocyanine Dye; vol. 23, No. 6, p. 411-423; 1975.
Dowd er al.; Evaluation of Methofologies Including Immunofluorescent Assay and the Polymerase Chain Reaction . . . ; Journal of Microbiological Methods; 35, p. 43-52; 1999.

* cited by examiner

*Primary Examiner*—Irene Marx
(74) *Attorney, Agent, or Firm*—Molly L. Sauter; Smith & Hopen, P.A.

(57) ABSTRACT

The present invention provides a method for the staining of fungi and *microsporidia* for observation with a light microscope based upon the presence of chitin in the composition of these organisms. With the method of the present invention a sample to be analyzed is treated with a solution of Ponceau S and Stains-all dye. The sample is then selectively decolorized and rinsed. The resulting sample is examined with a light microscope, or photographed for a permanent record, to identify the presence of a variety of microorganisms, to include fungi and *microsporidia*.

6 Claims, 10 Drawing Sheets

Staining of *Penicillium notatum*

Fig. 2 Staining of *Aspergillus niger*

Fig. 3 Staining of Bacteria versus Microsporidia

Fig. 4 Staining of *Cryptosporidium*

Fig. 5 Staining of Microsporidia

Fig. 6 Staining of *Rhizopus stolonifer*

Destaining of background

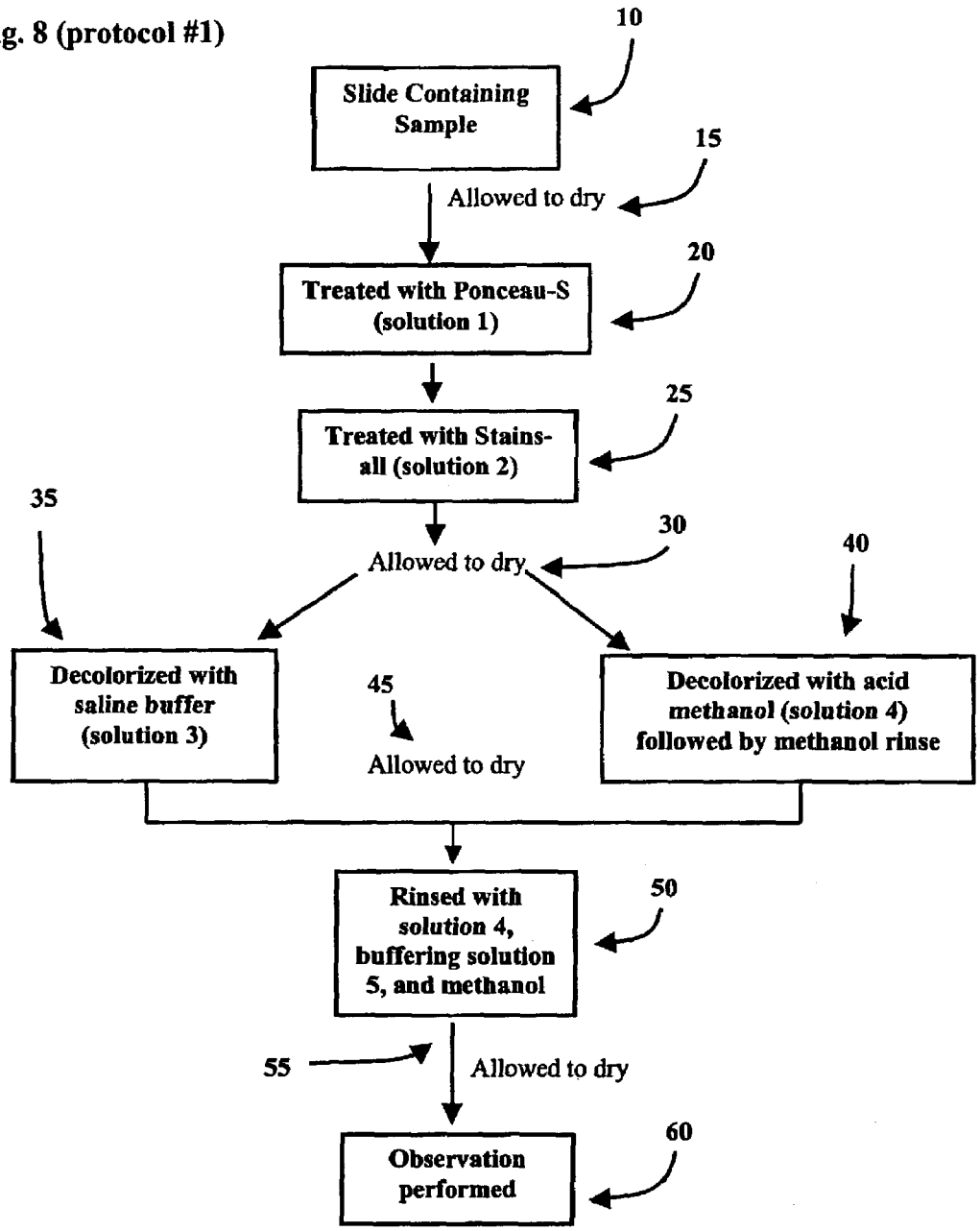
Fig. 8 (protocol #1)

Fig. 9 (Protocol #2)
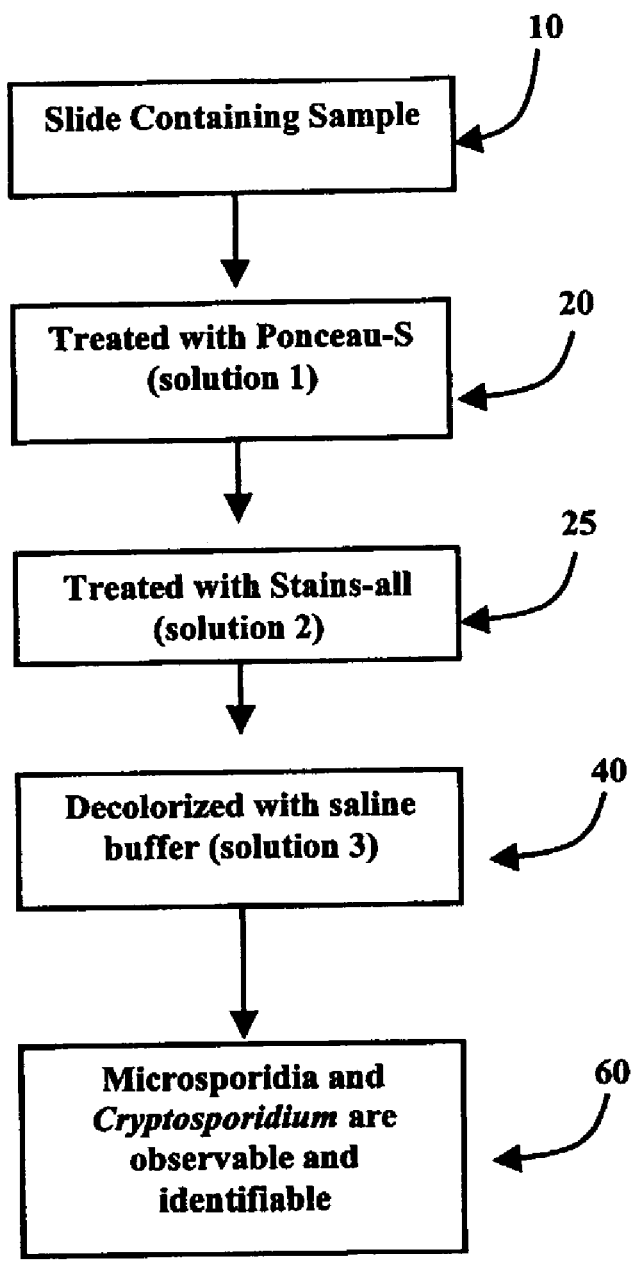

Fig. 10 (Protocol #3)
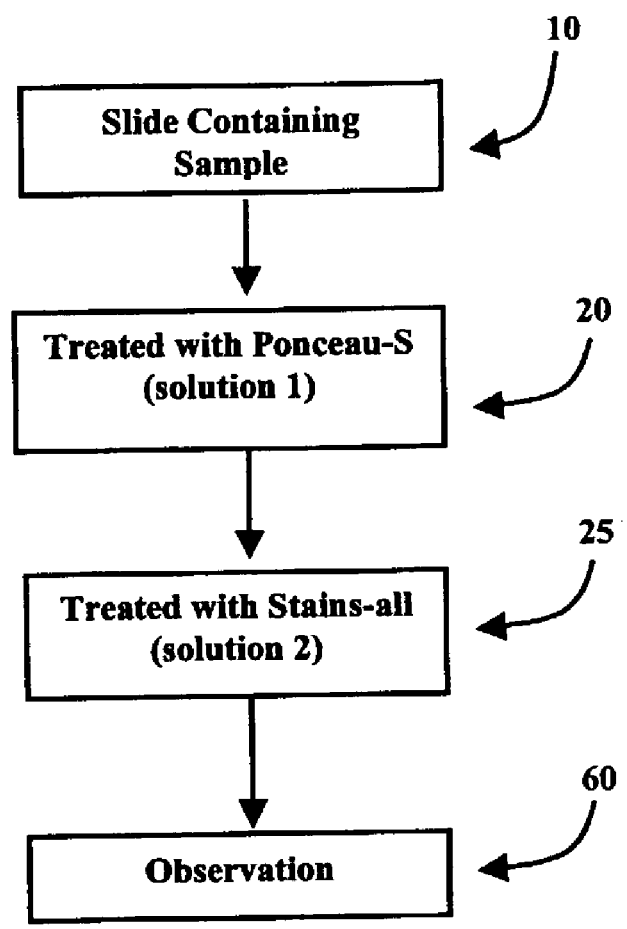

METHOD FOR STAINING FUNGI AND PROTOZOA

CROSS REFERENCE TO RELATED APPLICATION

This disclosure is a continuation-in-part of a co-pending disclosure of the same title by the same inventor, filed Apr. 29, 2002, bearing Ser. No. 60/319,214.

BACKGROUND OF INVENTION

This invention is a novel method of staining and detecting protozoa and fungi for observation under a light microscope, and with application to the qualitative and quantitative detection of *microsporidia* in environmental water samples.

Fungi and *microsporidia* can be differentiated from other microorganisms based on their chitin content. Current dyes used to stain chitin in fungi and *microsporidia* are based on fluorescent optical brighteners (Review by Ruchel et al., 2001), requiring a fluorescent microscope for observation. Details are not observable by this method.

A need exists in the art for the identification of the characteristic structures in microsporidian spores, including but not limited to thick spore walls, vacuoles, beltlike stripes and sporoplasms, that can be implemented using a light microscope, and recorded using a digital camera.

SUMMARY OF INVENTION

The present invention provides a method for determining the presence or absence of a microorganism in a sample suspected of containing a microorganism. In a preferred embodiment, a sample is provided to be analyzed, the sample is treated with a protein stain, and the sample is then treated with a cationic carbocyanine dye and examined for microorganisms.

In an additional embodiment, the protein stain used to treat the sample is Ponceau S. and preferably is a solution of 0.1% Ponceau S in 5% acetic acid in water.

In an additional embodiment, the cationic carbocyanine dye used to treat the sample is Stains-all, and preferably is a solution of Stains-all in methanol diluted 1:10 in a solution of deionized water, acetic acid, and methanol at 50:10:40.

In an additional embodiment of the present invention, an additional step of selectively decolorizing the sample is included. Selectively decolorizing the sample is facilitated through the application of a decolorizing solution. The decolorizing solution can be a solution of sodium dodecyl sulfate in phosphate buffered saline. Preferably the sodium dodecyl sulfate being 0.25% in phosphate buffered saline. Additionally, the decolorizing solution can be a solution of acid methanol, in a preferred solution of 50:10:40 deionized water, acetic acid, and methanol.

In an additional preferred embodiment of the present invention, an additional step of rinsing the sample prior to examining the sample in included. The rinsing step is facilitated by the application of a solution of acid methanol to the sample and subsequent treatment of the sample with a solution of phosphate buffered saline. Preferably the solution of acid methanol employed in the rinsing step is 50:10:40 deionized water, acetic acid, and methanol and the solution of phosphate buffered saline contains about 0.05% Tween 20.

In a preferred method of the present invention for the determination of the absence or presence of a microorganism in a sample suspected of containing a microorganism, a provided sample is treated with a solution of Ponceau S and Stains-all dye solution. The sample is then selectively decolorized, rinsed and examined for microorganisms.

A kit for detecting the presence of a microorganism is provided by the present invention in which is provided a protein stain and a cationic carbocyanine dyne.

In an additional embodiment of the kit, the protein stain is Ponceau S, and preferably a solution of 0.1% Ponceau S in 5% acetic acid in water.

In yet another embodiment of the kit of the present invention, the cationic carbocyanine dye is Stains-all, and preferably a solution of Stains-all in methanol diluted 1:10 in a solution of deionized water, acetic acid, and methanol at 50:10:40.

In an additional embodiment, the kit of the present invention includes a selective decolorizing solution. The decolorizing solution being sodium dodecyl sulfate in phosphate buffered saline, and preferably a solution of 0.25% sodium dodecyl sulfate in phosphate buffered saline. Additionally, the decolorizing solution can be a solution of acid methanol, preferably a solution of 50:10:40 deionized water, acetic acid, and methanol.

In yet another embodiment, the kit of the present invention includes a rinsing solution. The rinsing solution being acid methanol, preferably the solution of acid methanol is 50:10:40 deionized water, acetic acid, and methanol.

In another embodiment, the kit contains phosphate buffered saline solution. Preferably, the phosphate buffered saline solution being 0.05% Tween 20.

BRIEF DESCRIPTION OF DRAWINGS

For a fuller understanding of the nature and objects of the invention, reference should be made to the following detailed description, taken in connection with the accompanying drawings, in which:

FIG. 8 is a flow diagram demonstrating a method identified as Protocol 1 of the present invention.

FIG. 9 is a flow diagram demonstrating a method identified as Protocol 2 of the present invention.

FIG. 10 is a flow diagram demonstrating a method identified as Protocol 3 of the present invention.

DETAILED DESCRIPTION

Figure 1:
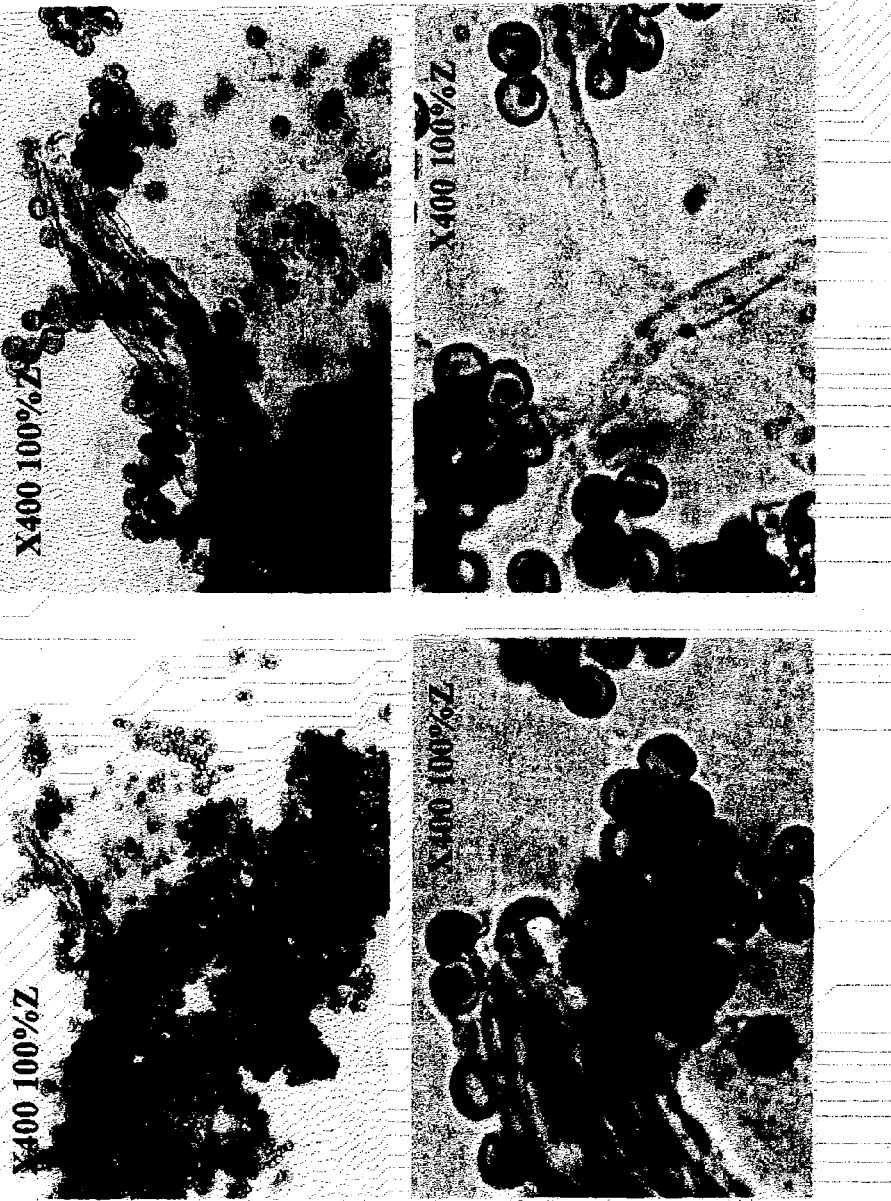
FIG. 1 are photographic slides of the staining of *Penicillium notatum using the present invention.*
Figure 2:
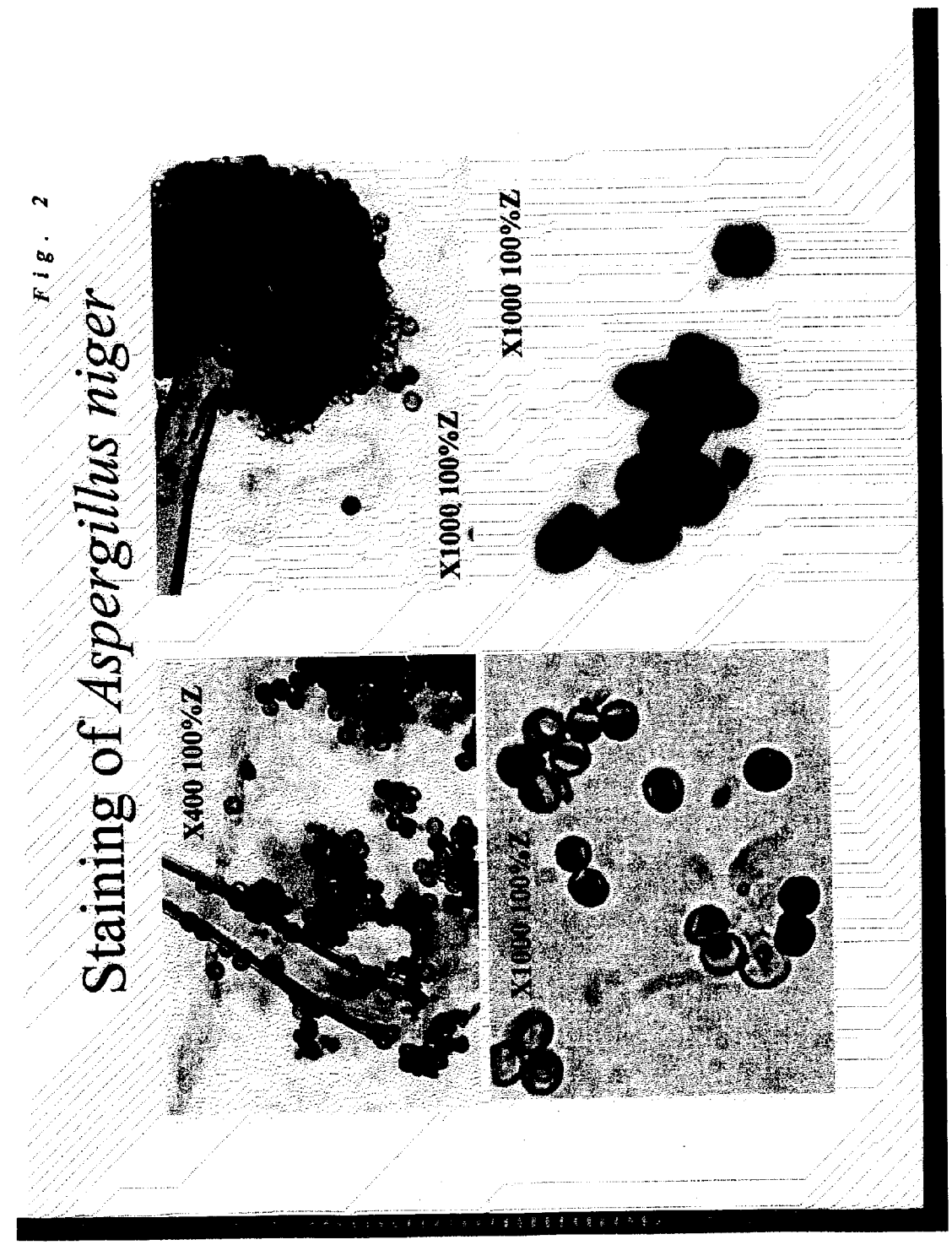
FIG. 2 are photographic slides of the staining of *Aspergillus niger using the present invention.*
Figure 3:
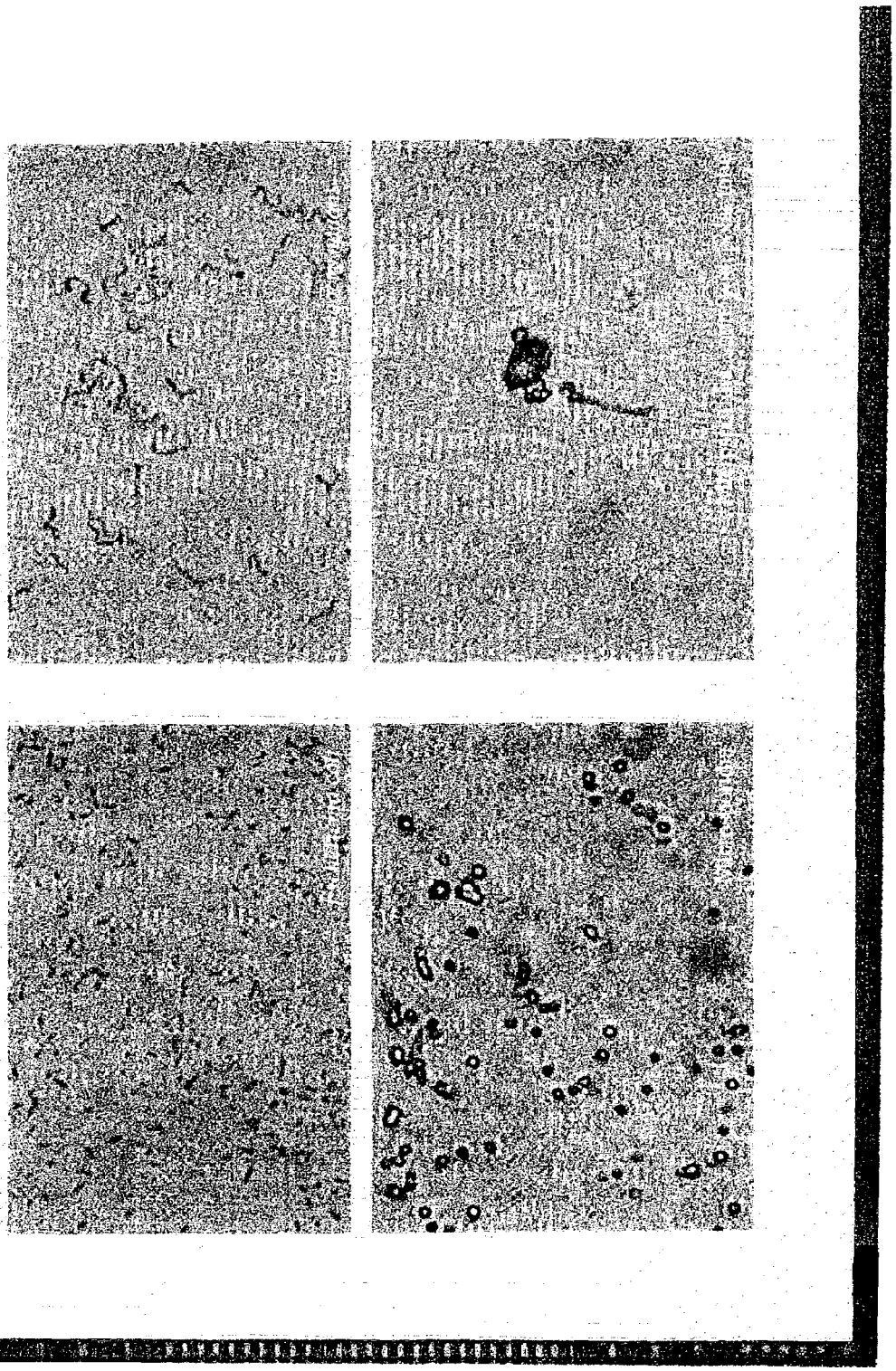
FIG. 3 are photographic slides of the staining of *Escherichia coli, streptocoocus mutans*, and *microsporidia* using the present invention.
Figure 4:
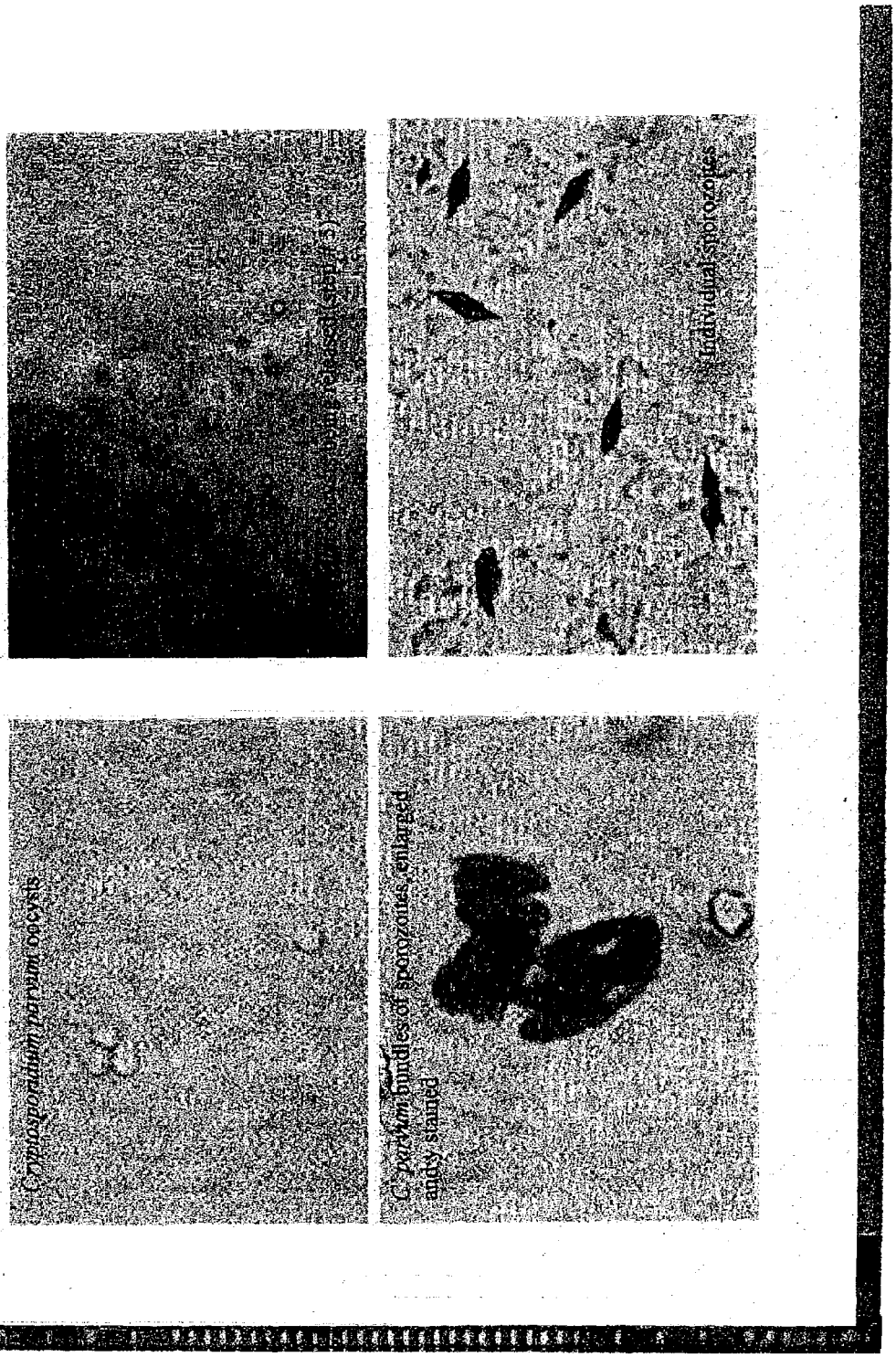
FIG. 4 are photographic slides of the staining of *Cryptosporidium* using the present invention.
Figure 5:
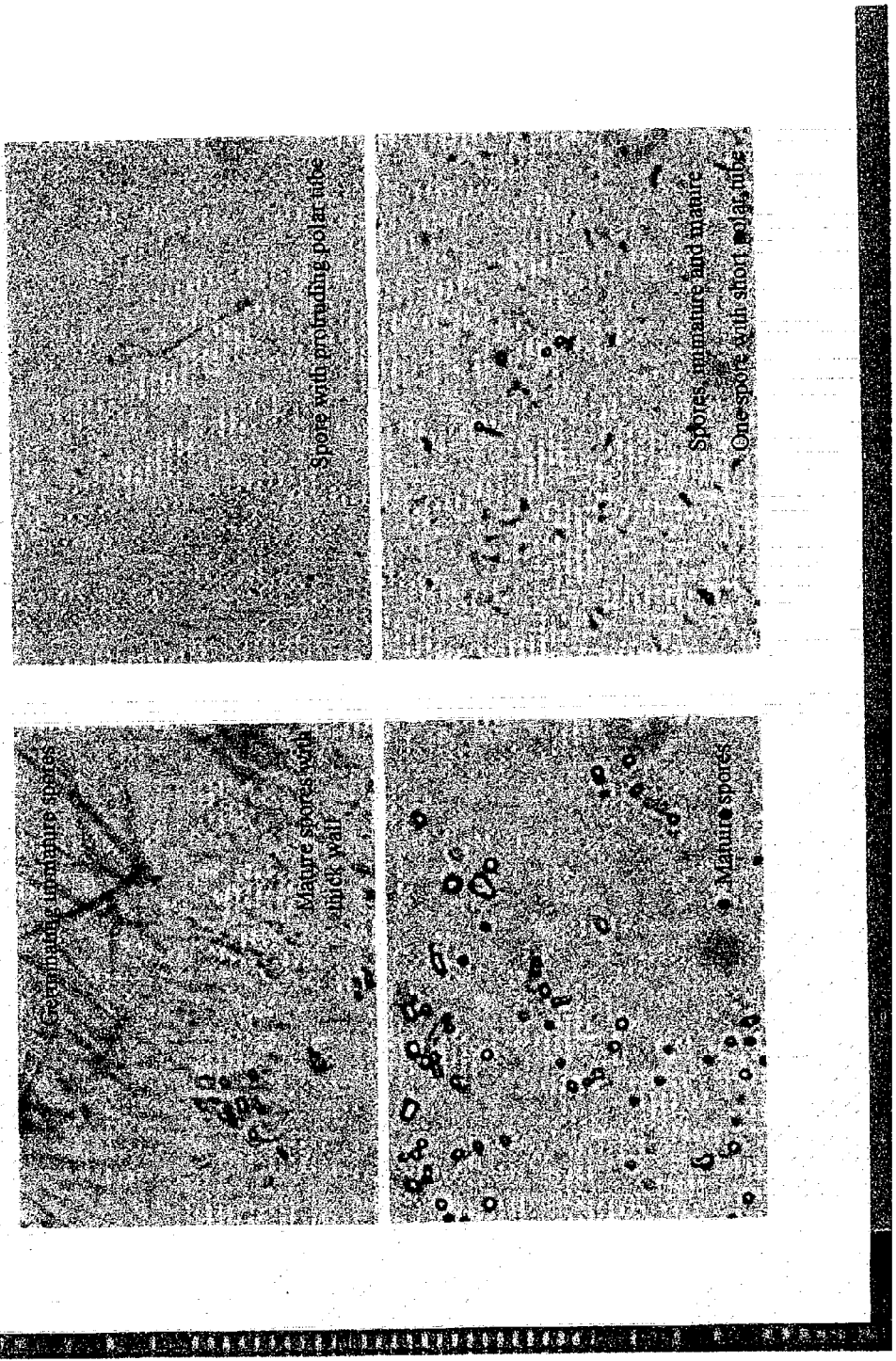
FIG. 5 are photographic slides of the staining of *Microsporidia* using the present invention.
Figure 6:
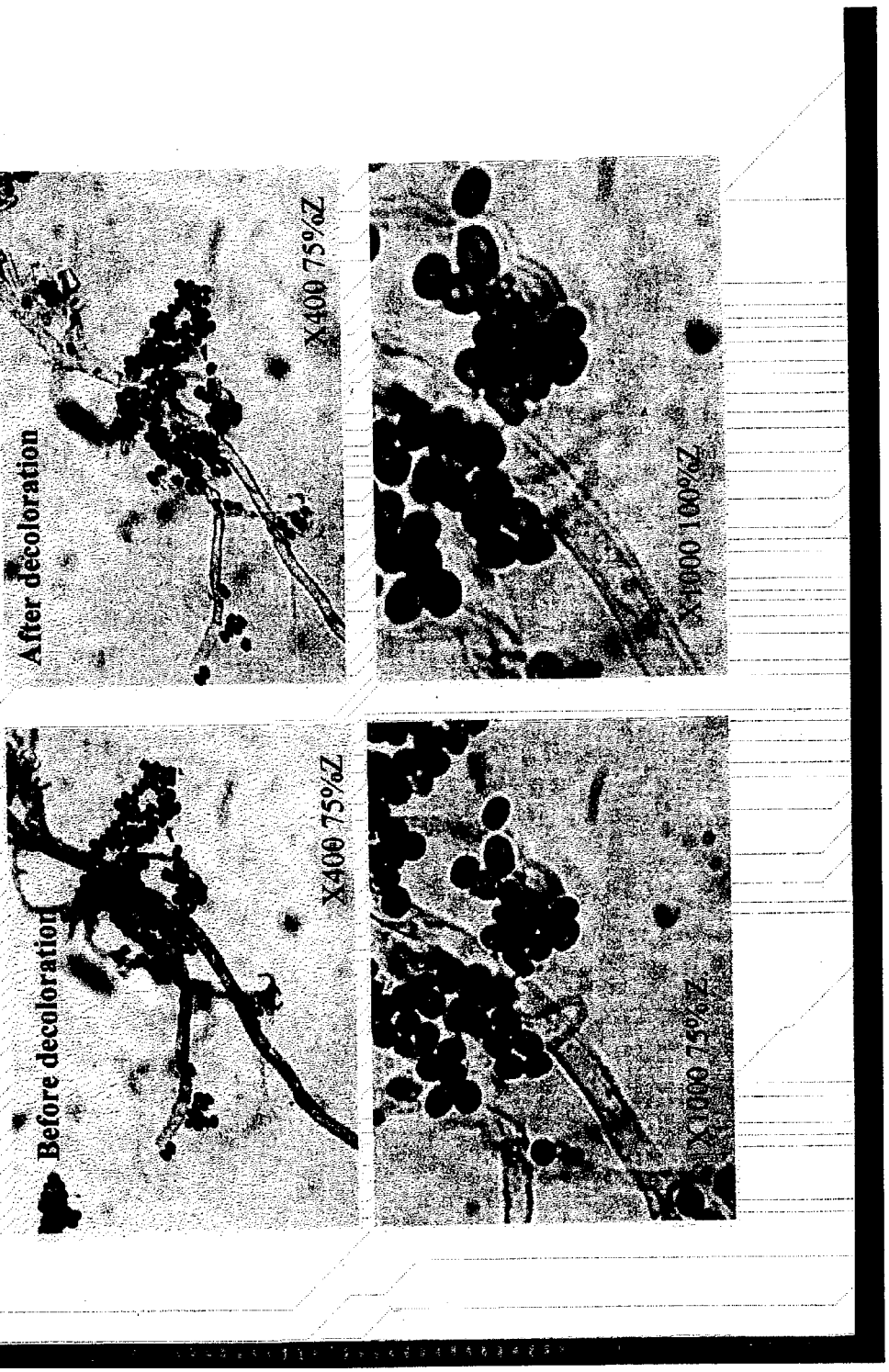
FIG. 6 are photographic slides of the staining of *Rhizopus stolonifer* using the present invention.
Figure 7:
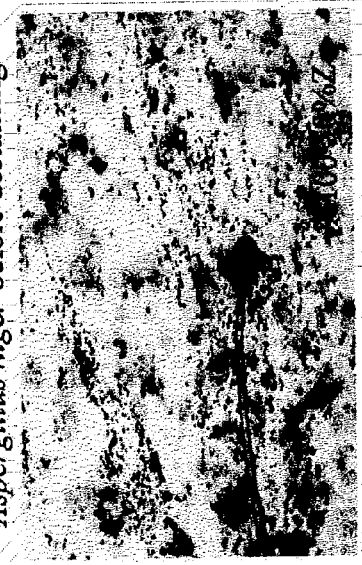
FIG. 7 are photographic slides of background destaining using the present invention.

The method of the present invention is based on three original observations made, including: (1) the strong binding of Ponceau S to chitosan, a derivative of chitin, and presumably other glucoaminoglycans; (2) the stable binding of Stains-all to Ponceau S; (3) the selective removal of dyes from non-chitin containing microorganisms by a PBS solution containing sodium dodecyl sulfate (SDS). Based on this method, convenient staining kits for fungi and *microsporidia* can be prepared and commercialized for use in research and clinical laboratories, in water analysis, and in food quality control. This method is also amenable to the staining of tissue sections, and automation for the routine analysis of a large number of environmental water samples.

New properties for the dye Stains-all have been observed in the laboratory setting. The dye complexes readily with the dye Ponceau S, causing a shift in the absorption spectrum of both the Ponceau S and the Stains-all dye. Additionally, new properties for the dye Ponceau S have been discovered. This dye is widely used for the staining of proteins in various applications, but it has been heretofore unknown in the prior art that this dye can stain strongly and permanently chitosan, a derivative of chitin. Subsequent to this finding, a protocol was invented to put these properties to use in the staining of fungi, and *microsporidia* as these organisms are known to contain chitin. Using this protocol, these organisms can be stained and identified, even in a complex mixture.

The preferred protocol of the present invention comprises the following steps (1) preparation of tissue section on slide, or application of the samples to be analyzed onto a microscopic slide, followed by drying; (2) sequential addition of the dye Ponceaus S and the dye Stains-all, followed by drying (3) selective decolorization by addition of SDS to destain non-chitin containing cells or microorganisms followed by drying; (4) sequential rinsing of the slide by acid-methanol, methanol, PBS containing Tween 20, then methanol. The drying step may be performed on a heating block (50° C.) to speed up the process. A light microscope is used for observation.

The staining method of the present invention uses Ponceau S and the Stains-all dyes. Ponceau S is also known as C.I. Acid Red 112, Ponceau Red and Ponceau X Extra. The chemical formula for Ponceau S is 3-hydroxy-4((2-sulfo-4-((-4-sulfophenyl(azo)phenyl-) azo) 2,7 naphthalenedisulfonic acid tetrasodium salt. The dye Stains-all, a cationic carbocyanine dye, [7423-31-6] 1-Ethyl-2-[3-(1-ethylnaphtho[1,2-d]thiazolin-2-ylidene)-2-methylpropenyl]naphto[1,2-d]thiazolium bromide, is a sensitive stain for various biochemical components including nucleic acid, hyaluronic acid phosphoproteins and non-phosphorylated proteins, and acid mucopolysaccharides.

Different colors are obtained depending on the nature of the biochemical component. The Stains-all dye interacts with these compounds forming different complexes absorbing at various wavelengths (Kay et al., 1964; Green et al., 1973). Application of the Stains-all dye is limited to the electrophoretic characterization of nucleic acids, proteins (phosphorylated and non-phosphorylated), and substituted polysaccharides in polyacrylamide or composite agarose and polyacrylamide gels (Green et al., 1973; Dalberg et al., 1969; Bader et al., 1972). Stains-all can be used to simultaneously stain nucleic acids, proteins, conjugated proteins and polar lipids (Green, 1975). Although, Stains-all is a sensitive and potentially useful as a differential dye, it has not been used to stain microorganisms. One disadvantage associated with the dye is that it fades rapidly.

Thus, the dye Stains-all used in combination with Ponceau S to stain *microsporidia* and fungi produces new and unexpected results. By staining with Ponceau S alone, it is not possible to identify these organisms because Ponceau S stains both proteins and polysaccharides in pink or red. As stated above, Stains-all can differentially stain a number of macromolecules, but has not yet been used to stain microorganisms. This dye is also unpopular due to its propensity to fade away. According to the invented protocol, Ponceau S is used first to stain proteins and more strongly chitin before the addition of Stains-all. The latter dye complexes in situ with Ponceau S, enhancing the coloration and providing different tints due to its binding to other components. The resulting effect is a stable coloration, withstanding the selective decolorization step, and allowing the detection and analysis of fungi and *microsporidia*, even in a complex mixture of microorganisms.

Protocol #1

Protocol #1 as shown in FIG. 8, the preferred staining method as taught by the present invention comprises five solutions: (1) solution of 0.1% Ponceau S in 5% Acetic acid (Ponceau S, Sodium salt is a product of Sigma Chemical Company, St. Louis, Mo.); (2) solution comprising a mixture (1:9, v:v) of 0.2% Stains-all (Stains-all is a product of Acros Organics, NJ) in Methanol (stock solution), which is diluted 1:10 in a solution of acid-methanol (solution 4) before use; (3) solution comprising 0.25% SDS in PBS; (4) solution of Deionized water:Acetic Acid: Methanol (50:10:40); (5) solution of PBS containing 0.05% Tween 20. Preferably, the solutions are supplied in drop-dispensing bottles to simplify the procedure. Additional requirements include Methanol, a heating block set at 50° C., a light microscope, and a digital camera to take micrographs of the slides (Olympus C3030Z or higher).

In an exemplary method, protocol # 1, of the present invention, comprises:

Application of the sample: apply tissue section or aqueous sample containing microorganisms (ex. suspension in PBS) is applied onto a microscopic slide 10, and allowed to dry 15 at room temperature or on a heating block (50° C.);

Staining: one or more drops of solution 1 20 is added to cover the sample for 10 sec, followed by 2 or more drops of solution 2 25 to cover the sample for 10 sec, pouring off the excess solution and drying 30 at room temperature or on a heating block;

Selective decolorization: 2 or more drops of solution 3 are added to cover the sample 35, and left to stand for approximately three minutes until decolorization of extraneous materials. Then the slide is permitted to air-dry 45 at room temperature or on a heating block (50° C.). Alternatively, an equal volume of acid methanol (solution 4) is added 40 and left in contact for 10 sec, followed by pouring off the excess and rinsing with methanol; Rinsing: The slide is sequentially rinsed 50 with solution 4 added dropwise to cover the sample for 10 sec, followed by methanol, then with solution 5 added dropwise to cover the sample for 10 sec, followed by three rinses with methanol and air-drying 55. Observation is performed on the light microscope 60. Microspodian spores are observable at X40 based on their darkly stained spore wall, with more characteristics visible at higher magnification.

There are substantial advantages to the present invention. Sensitivity is enhanced. Using protocol # 1, differential coloration of fungi, *microsporidia*, and *Cryptosporidium* is obtained, and detected even in the presence of host cells or other microorganisms, without the need for purification. Non-chitin containing cells such as bacteria (both Gram− and Gram+) and mammalian cells are selectively decolorized by solution 3 in protocol # 1. No purification of chitin-containing organisms is needed in the present method, as they are apparent and stand out even in complex mixtures such as septic tank sample, or in presence of bacteria and mammalian cells. Only a light microscope is needed for observation.

Protocol#2

As shown with reference to FIG. 9, it is within the scope of the present invention to modify protocol #1 to establish protocol # 2, in which samples are not heated dry before the sequential addition of the dyes at steps 20 and 25, and observation is made upon addition of a drop of solution 3 (SDS) 35 in the middle of the sample. With protocol #2, *microsporidia* and *Cryptosporidium* can be identified in the same sample 60. The immature microsporidian spores are easily detectable as they are enlarged and elongated while staining in red. *C. parvum* sporozoites, individual or in bundle, stained by protocol # 2, are dramatically enlarged and stained in a distinctive red golden brown. Oocysts are released from host cells. Thick walled oocysts do not stain but are apparent, whereas immature oocysts stained in dark red, some of which are enlarged showing stained merozoites or sporozoites in red golden brown. Protocol #2 is allows for the observation of the release of microsporidian spores from parasitophorous vacuoles, followed by a gradual migration of these spores to the periphery of the drop of PBS solution containing SDS, which is accompanied by thegermination or elongation of immature spores. Although *Cryptosporidium* does not contain chitin, some staining was observed probably due to the presence of complex carbohydrates such as glucoaminoglycans. Using protocol # 2 to stain mammalian cells infected with *C. parvum*, intracellular stages, and thin wall-oocysts are released from the infected mammalian cells and stained in a distinctive red golden brown color at the selective decoloration step. Hence, *microsporidia* and *Cryptosporidium* can be recognized when present in the same sample when stained by protocol # 2.

Protocol#3

In is within the scope of the present invention to modify protocol #1 to establish protocol # 3 in which other microorganisms, such as bacteria, are differentially stained. In protocol # 3, the selective decoloration step 35 or 40 is omitted. Apparent differences can be observed between different strains of *E. coli* By omitting the selective decoloration step, as in protocol # 3, the use of the dyes Ponceau S and Stains-all can be extended to all other microorganisms for detection based on their difference in size, shape and coloration, properties that can be photographed with a digital camera. For instance, apparent differences are observed with various *Escherichia coli* strains. It is noteworthy that a number of modern biosensors are being developed to analyze microorganisms based on morphological characteristics.

In summary, the invention is useful for the analysis of fungi, and especially useful for the detection of *microsporidia* and *Cryptosporidium*, in pure sample as well as in complex mixture such as clinical and environmental samples, and perhaps also foodstuffs that do not contain chitin. With the invented method, it is possible to detect *microsporidia* and *Cryptosporidium* in septic tank samples, and samples of organisms retained on 0.45 um filter from water samples from various sources or sedimented by centrifugation, as well as infected live or formalin-fixed cells and tissues. Additionally, based on the properties mentioned above of the dyes Ponceau S and Stains-all, the present staining method can be modified to stain other microorganisms, which can then be identified based on their size, shape and coloration. Currently, the most specific tests for the identification of *microsporidia* in water samples are based on genetic method, for example PCR for the amplification of specific genes (Dowd et al., 1999). In this method, the organisms have to be isolated, and their DNA extracted. The sensitivity of the method depends on the efficacy of recovery of the spores from environmental samples by immunomagnetic beads, while DNA isolation from spores is time consuming. This taken with the cost associated with PCR analysis, it is impractical to use genetic tests to routinely and systematically monitor water pollution by *microsporidia*. The staining method developed in the present invention can be used as a presumptive screening test to identify samples contaminated with *microsporidia* and/or *C. parvum* for further confirmation by genetic analysis. The entire staining procedure takes less than 30 minutes.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

The invention claimed is:

1. A method for determining the presence or absence of a chitin-containing microorganism in a sample suspected of containing a chitin-containing microorganism, the method comprising the steps of:
 providing a sample suspected of containing a chitin-containing microorganism to be analyzed;
 treating the sample with 3-hydroxy-4((2-sulfo-4-((-4-sulfophenyl(azo)phenyl)azo) 2,7 naphthalenedisulfonic acid tetrasodium salt stain to stain the chitin of the chitin-containing microorganism;
 treating the sample with 1-Ethyl-2-[3-(1-ethylnaphtho[1,2-d]thiazolin-2-ylidene)-2-methylpropenyl]naphto[1,2-d]thiazolium bromide dye, said dye binding to the 3-hydroxy-4((2-sulfo-4-((-4-sulfophenyl(azo)phenyl)azo)2,7 naphthalenedisulfonic acid tetrasodium salt stain to form a light-stable complex; and
 examining the sample with a light microscope to identify the presence of chitin-containing microorganisms in the sample, wherein the stained chitin-containing microorganisms are observable in the light microscope.

2. The method of claim 1, further comprising prior to the examining step, the step of selectively decolorizing the sample.

3. The method of claim 2, wherein the step of selectively decolorizing the sample further comprises the steps of:
 applying a decolorizing solution to the sample; and
 rinsing the sample.

4. The method of claim 3, wherein the decolorizing solution is 0.25% sodium dodecyl sulfate in phosphate buffered saline.

5. The method of claim 3, wherein the step of rising the sample comprises the application of a solution of acid, methanol, and water in the ratio of 10:40:50, respectively.

6. A method for determining the presence or absence of a chitin-containing microorganism in a sample suspected of containing a chitin-containing microorganism, the method comprising the steps of:
 providing a sample suspected of containing a chitin-containing microorganism to be analyzed;

treating the sample with 3-hydroxy-4((2-sulfo-4-((-4-sulfophenyl(azo)phenyl)azo) 2,7 naphthalenedisulfonic acid tetrasodium salt stain to stain the chitin of the chitin-containing microorganism;

treating the sample with 1-Ethyl-2-[3-(1-ethylnaphtho[1,2-d]thiazolin-2-ylidene)-2-methylpropenyl]naphto[1,2-d]thiazolium bromide dye, said dye binding to the 3-hydroxy-4((2-sulfo-4-((-4-sulfophenyl(azo)phenyl)azo)2,7 naphthalenedisulfonic acid tetrasodium salt stain to form a light-stable complex; and selectively decolorizing the sample;

rinsing the sample; and examining the sample with a light microscope to identify the presence of chitin-containing microorganisms in the sample, wherein the stained chitin-containing microorganisms are observable in the light microscope.

* * * * *